United States Patent
Shields

(10) Patent No.: US 6,524,279 B1
(45) Date of Patent: Feb. 25, 2003

(54) SHIELDED ASSEMBLY FOR BLOOD COLLECTION IN VACUUM TUBES

(76) Inventor: Jack W. Shields, 1950 Las Tunas Rd., Santa Barbara, CA (US) 93103

( * ) Notice: Subject to any disclaimer, the term of this patent is extended or adjusted under 35 U.S.C. 154(b) by 157 days.

(21) Appl. No.: 09/752,756

(22) Filed: Dec. 22, 2000

(51) Int. Cl.⁷ ................................................. A61M 5/32
(52) U.S. Cl. ...................................... 604/198; 604/412
(58) Field of Search ................................ 604/410, 411, 604/412, 413, 414, 415, 198; 600/576, 577, 583

(56) References Cited

U.S. PATENT DOCUMENTS

| | | | |
|---|---|---|---|
| 3,706,305 A | * 12/1972 | Berger et al. ............... | 422/102 |
| RE33,585 E | * 5/1991 | Harber et al. ............... | 604/198 |
| 6,013,037 A | * 1/2000 | Brannon ..................... | 600/576 |

\* cited by examiner

Primary Examiner—Henry C. Yuen
Assistant Examiner—Mahmoud Gimie

(57) ABSTRACT

A needle assembly operable for the transfer of blood from a blood vessel to a vacuum tube contained within a vacuum tube holder. The assembly includes: (a) a first needle holder having a leading end and a trailing end and a hollow conical body portion therebetween; (b) a first hollow bore needle having a sharp beveled tip at a leading end thereof, a hub at a trailing end thereof, and a shank therebetween, the hub being disposed within the conical cavity and releasably attached to the leading end of the first needle holder; (c) a rigid tube having a leading end affixed to the hub of the first needle, a trailing end and a length therebetween, the rigid tube having an axial bore coextensive with the length of the rigid tube; and (d) a second hollow bore needle having a leading end disposed within the axial bore of the rigid tube and affixed to the trailing end of the rigid tube. The second needle has a trailing portion that includes a sharp trailing end projecting from the trailing end of the rigid tube. The trailing portion further includes attachment means operable for releasably attaching the second needle to the vacuum tube holder.

5 Claims, 3 Drawing Sheets

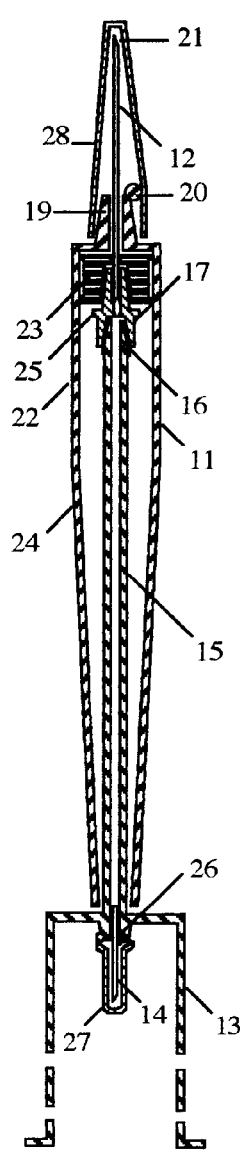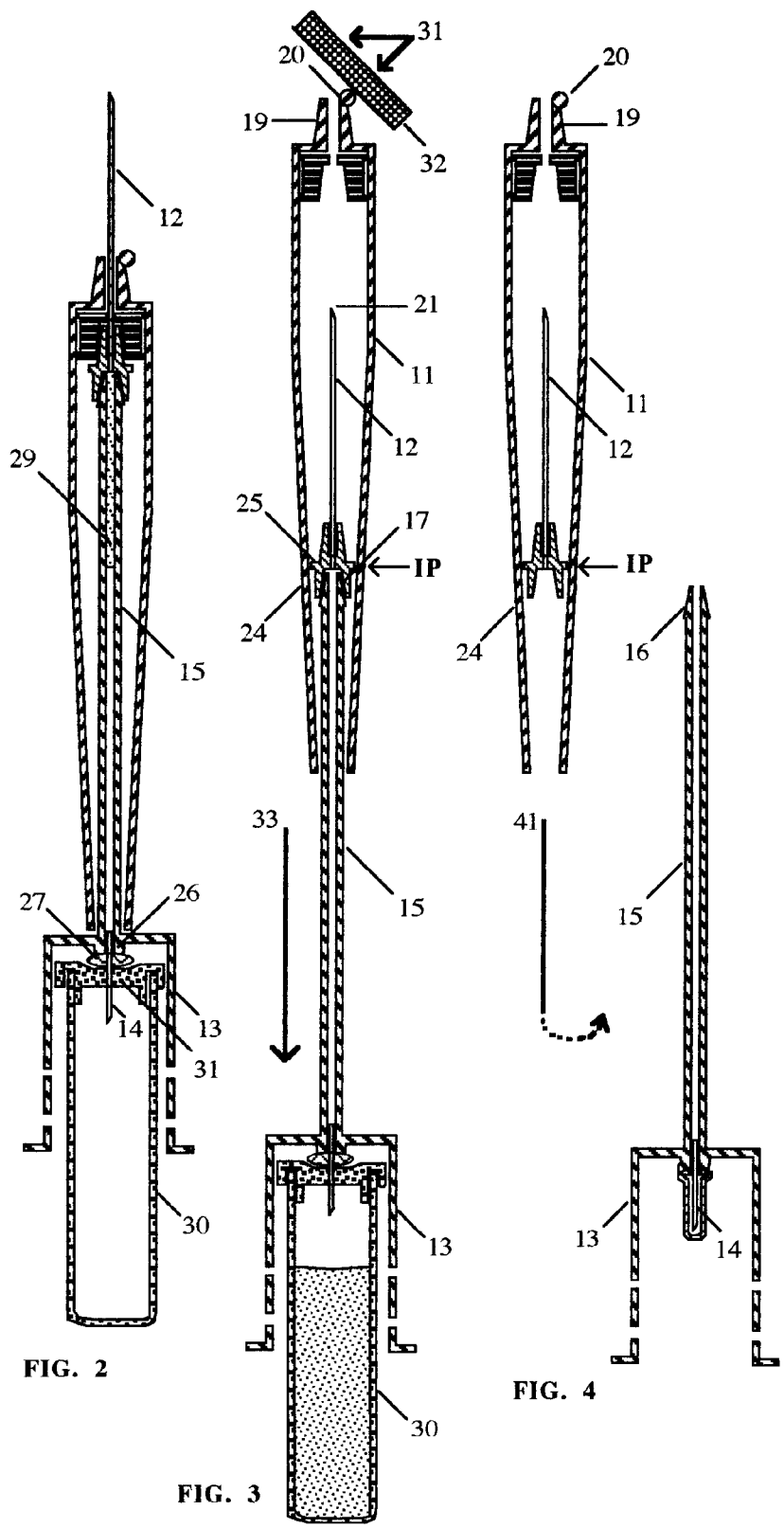
FIG. 1
FIG. 2
FIG. 3
FIG. 4

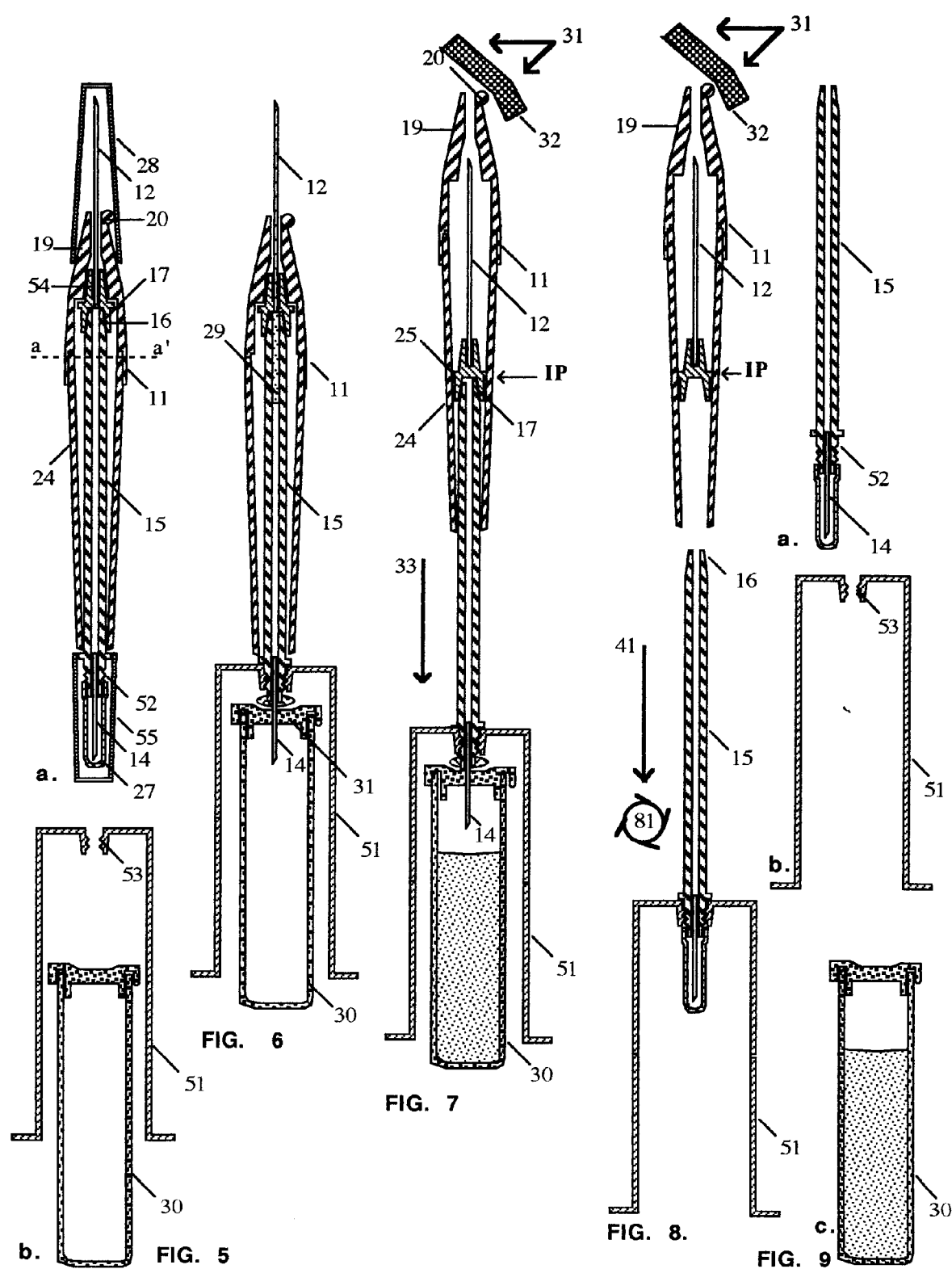

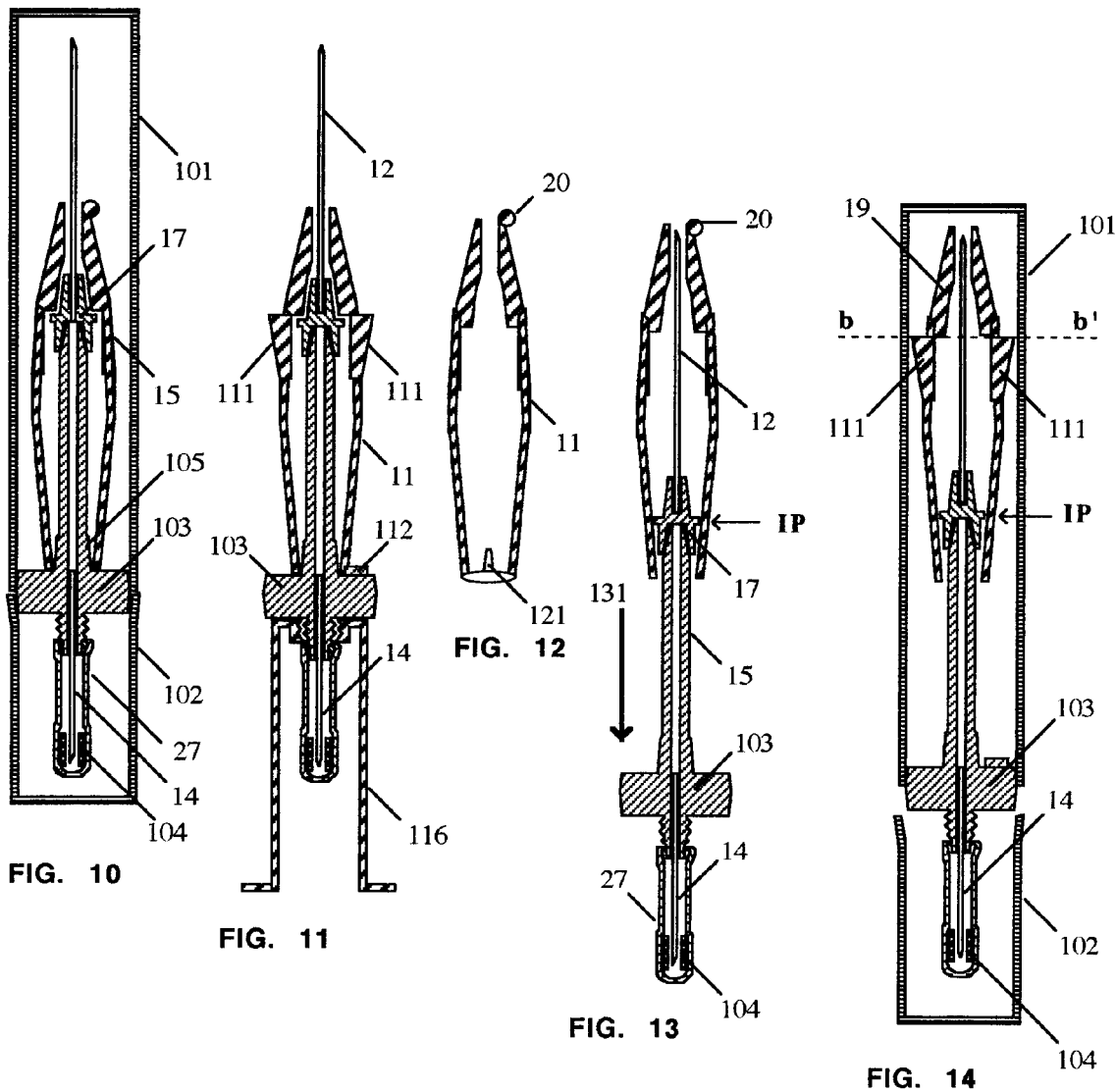

SHIELDED ASSEMBLY FOR BLOOD COLLECTION IN VACUUM TUBES

BACKGROUND OF THE INVENTION

1. Field of the Invention

A venous blood collection assembly via vacuum tubes for conveniently minimizing accidental needlesticks in users and maximizing safety for patients.

2. Prior Art

Since the recognized advent of the acquired immunodeficiency syndrome (AIDS) in 1981 and recognition that other bloodborne viruses, such as hepatitis B virus (HBV) and hepatitis C virus (HCV), are being transmitted to healthcare workers (HCWs) at alarming rates via accidental needlestick exposures to blood or other body fluids, maximal efforts toward preventing such exposures have been stressed by the medical device industry, as well as the U.S. Government. Over a thousand patents have issued or pend for safer devices capable of shielding HCWs from an estimated 800,000 accidental needlesticks during the use of approximately six billion hollow steel needles used annually in US patient care. It is expected that within nine months after our President's signature of the Needle Stick Safety Prevention Act on Oct. 6, 2000, the common use of safety engineered needlestick prevention devices will be mandatory throughout the USA.

In the field of assemblies patented and pending for blood collection via vacuum tubes, the following prior art seems cogent:

Needles originally designed for blood collection into vacuum tubes comprised a leading ±1.0"20 to 23 G first needle sharp on the leading end and a second ±0.5"20 G needle sharp on the trailing end permanently affixed into a single unit by a hub having a slip connector on the leading end for attachment of a protective scabbard for the first needle and a threaded connector on the trailing end for reversibly affixing the second needle into the cavity of a vacuum tube holder before insertion of the vacuum tube. Also, the trailing end of the hub was made with a slip connector for a protective scabbard for the second needle, such that the open ends of each scabbard abutted one to another and could be sealed further with a breakable label for the assembled sterilized contents in a very compact package. Later, was added an elastomeric tubular sleeve with a closed trailing end and an open leading end affixed by elastic recoil to the trailing end of the hub holding both needles. The purpose of this air-tight sleeve was to prevent blood leakage into the cavity of the holder before the vacuum tube is inserted, to minimize leakage between insertions of more than one vacuum tube, and to minimize leakage after the last vacuum tube has been extracted from the cavity of the vacuum tube holder. When it became obvious that neither the first, nor the second needle should be manually recapped with its originally supplied protective scabbard, the lids of containers for used sharps in blood collection stations and on portable blood collection trays were modified with special receptacles which allowed HCWs to safely detach the hub holding two exposed sharp needles by unscrewing the trailing end of the hub from the vacuum tube holder into the cavity of the sharps container, using one hand while doing so.

Following blood collection apart from handy sharps containers with appropriate needle removal receptacles, it became obvious that the exposed first needles are hazardous for patients, phlebotomists and other HCWs. The early remedies were vacuum tube holders with outer sleeves which slide forward and lock after use to protect finger access to the bevel of the first needle used to withdraw venous blood. Such devices proved cumbersome, required two hands to activate the protective sleeve after the leading needle is withdrawn from a patient's vein and require disposal of the vacuum tube holder containing the first needle and the second needle which punctures the leading cap on vacuum tubes.

Commercial development then turned toward intrinsic means for shielding the bevel and shank of the first needle, especially by methods applicable to syringe/needle combinations used for giving injections. A variety of devices of two fundamental types evolved rapidly.

The first type basically comprises a variety of sleeves permanently attached to the leading part of the needle which can be finger-manipulated to safely cover the bevel and shank after the needle is withdrawn from the vein of a patient. One of the first was the ICU Medical Blood Collection Needle twice usual length, over which a sliding tube is manipulated to lock over and shield the leading bevel and shank after withdrawal from a vein, along with a trailing needle whose hub screws into the leading end of a standard vacuum tube holder. Although the vacuum tube holder could be used again with another similar needle, the length of the needle beyond the vacuum tube holder made venous access awkward for many phlebotomists, and provided no intrinsic means for safe disposal of the trailing second needle. To obviate such problems Sims-Portex developed the Needle-Pro™. a singly hinged plastic shield permanently attached to the first needle hub which swings from one side to cover and lock in the exposed needle shank and bevel. Becton-Dickinson developed a doubly hinged device, called Safety-Glide™, attached similarly which slides forward and locks to enclose and protect the first needle with straight forward finger action. Others developed compressed spring operated systems whose latches permitted the spring extension of protective caps over the first needle bevel after use. Still others, such as Retractible Technologies developed the Vanish Point™ (U.S. Pat. No. 5,423,758) spring-operated device attached to the trailing end of the first needle hub which, with forward pressure exerted on an inserted sleeve by means of a trailing hinging cap on the vacuum tube holder, releases the spring such that the first and second needles vanish, along with their common hub, into the confines of the cavity in the holder whose trailing end is closed by the hinging cap.

The second type of intrinsic means for shielding the first needle is exemplified in the Bioplexus Puncture Guard® system which embodies an obturator with a blunt tip which is passed through the bore of the first needle to extend beyond the sharp tip of the needle bevel and locked in place by a latch mechanism inside the needle hub, when the user exerts increased forward pressure on a vacuum tube inserted into the vacuum tube holder, after final use for blood collection.

Currently in California, where the use of safety-engineered needles for preventing needlesticks is universally directed under CPL 2-2.44D (Nov. 5, 1999), the use of the Becton-Dickinson Safety Glide™ or Bioplexus Puncture Guard® protectors for the first needles, in conjunction with modified reusable vacuum tube holders appears most common for blood collection. The embodied modifications in the vacuum tube holders consist of differing manually activated latch mechanisms for expanding the diameter of the leading aperture in the vacuum tube holder, such that the threaded trailing end of the first and second needle hub can be dropped through a large diameter aperture through the top of a sharps container when convenient, and the vacutainer holder can be reused subsequently.

The Becton-Dickinson Safety Glide™ system retains at least three potential hazards: (a) the leading needle must be withdrawn from a patient's vein before the needle can be protected; (b) the latch for releasing the trailing needle from the reusable vacutainer holder is not always easy to operate; and (c) the bulk and external leading diameter of the modified Vacutainer™ holder provides a suboptimal angle of venous access by and venous withdrawal of the leading needle. The Bioplexus Puncture Guard® system retains at least three potential hazards: (a) advancement of the obturator through the leading needle bore before the needle is withdrawn could cause venous injury; (b) the latch in the reusable Drop It® vacuum tube holder for releasing the trailing needle sometimes fails, such the obturator and the leading needle bevel are further advanced into the vein of the patient with actual vein injury; and (c) poor alignment of the leading needle bevel in relation to the latch on the Drop It® may increase the angle of venous angle of access and withdrawal with the bevel of the needle always upward. Both systems present reusable vacuum tube holders whose use is limited to recommend numbers of uses and which are not easy to clean after use.

The instant invention differs from all the prior art in the following respects:

(a) The blood collection needle and the vacuum tube holder are fabricated in a single assembly wherein the first needle slidingly contained in a small diameter needle holder is linked by means of breakable female slip connection to a mating male slip connection on the leading end of a long rigid transparent tube permanently embodied into the leading end of a vacuum tube holder wherein the second needle is permanently housed such that the lumen of the first needle is confluent with that of the second until the mating slip connections are broken after use for collecting blood into one or more vacuum tubes. Because the second needle is permanently embodied and recessed in the leading cavity of the vacuum tube holder and the first needle hub becomes trapped inside the needle holder during withdrawal and twisting of the long rigid tube embodied on the leading end of the vacuum tube holder, the beveled tip and shank of neither needle is exposed to cause injury to a user, a patient or a bystander after use of the assembly which becomes safely disposable in two parts, neither of which can be reused; but are shielded immediately after use, such that immediate disposal into a sharps container is not critical.

(b) Embodiment of a slip connection between the first needle hub and a rigid tube for guiding the thrust and retraction of the first needle hub into a predetermined site of wedge impaction in the trailing conical bore of the first needle holder, as taught in Shields U.S. Pat. No. 5,007,901 (Apr. 16, 1991), U.S. Pat. No. 5,401,250 (Mar. 28, 1995), U.S. Pat. No. 6,126,621 (Oct. 03, 2000), is not taught or claimed in any of the cited prior art applicable to blood collection via vacuum tubes.

(c) Embodiment of a leading dorsal tether or head projection on the first needle holder, as taught in Shields U.S. Pat. No. 5,350,368 (Sep. 27, 1994), U.S. Pat. No. 5,401,250 (Mar. 28, 1995), U.S. Pat. No. 5,858,004 (Jan. 12, 1999) for holding pressure over a vein and stabilizing the leading end of the needle holder such that the needle can be withdrawn comfortably and safely from a vein without exposure of the bevel or shank during or after withdrawal, is not taught or claimed in any of the cited prior art applicable to blood collection via vacuum tubes.

(d) Embodiment of a syringe piston in the needle holder for stabilizing the thrust of the first needle and preventing blood leakage from the needle holder after the needle is retracted into the bore is not taught or claimed in any of the prior art cited.

(e) It would appear from the prior art cited that sleeves which slide over the first needle or over the vacuum tube holder and the Vanish Point® system resemble the instant invention most closely in purpose. However, none of the mechanical details patented in each are embodied in this innovative system.

SUMMARY

The object of this invention is to provide a simple, efficient and cost-effective means to make blood collection into vacuum tubes as safe as possible for patients and HCWs. Outstanding advantages over the Prior ART might be listed as follows:

1. Being a completely integrated assembly, the user opens one sterile package and everything is ready for use, except for removal of the disposable scabbard initially supplied for shielding the first needle before venous insertion.

2. Lacking springs, latches and sliding parts necessitating use of both hands, the assembly should prove relatively free from mechanical and user failures.

3. Owing to a relatively small diameter of the leading end of the needle holder compared with that of the vacuum tube holder, a superior and low angle of needle approach to and withdrawal from a selected vein will be achieved for the benefit of the patient and for preventing venous injury, especially in small or hard-access-veins.

4. Owing to a leading means for stabilizing the leading end of the first needle holder while simultaneously holding finger pressure over the selected venipuncture site, the bevel and shank of the first needle will never be exposed during or after venous withdrawal. Equally important, with the needle already shielded, finger pressure with the non-dominant hand can be sustained as long as optimal for preventing vein injury and bleeding; while the dominant hand can be used for sundry purposes.

5. Owing the permanent embodiment of the second needle in the leading end of the vacutainer holder, the bevel and shank of this needle are permanently recessed, such that needlestick injury is impossible, except in instances wherein the internal diameter of the vacutainer is greater than that of the finger of a HCW who sticks a finger into the cavity for no purposeful reason or some child is given a used holder to play with. This problem is soluble by making vacuum tube holder internal diameters more fitting to the external diameters of currently inserted 7.0 mL or pediatric vacuum tubes, instead of expanding their cap diameters to fit holders for archaic 10 mL. vacuum tubes of similar length.

6. The current industry approach to (5) is that reuse of vacuum tube holders ±50 times saves patient and user costs appreciably and is convenient in blood collecting stations wherein space for disposal of used ones in sharps containers can be rapidly overloaded by their bulk, Those pursuing patient, as well as user safety, might rebut as follows:

The elastomeric cap covering the bevel and shank of the second needle embodied into, or temporarily inserted into a vacuum tube holder, was designed to stop leakage of venous blood under 5–20 cm. of hydrostatic venous pressure through the trailing end of the blood collection assembly until an inserted vacuum tube accelerates retrograde flow via the bore of the second needle. However, after the first puncture of the trailing end of the elastomeric cap occasioned by insertion of the first vacuum tube and others with or without diluents essential to the analysis of collected whole blood, the elastomeric cap will leak more and more venous blood under ambient venous pressure into the cavity of the vacuum tube holder, more or, less proportional the number of times the trailing end of the elastomeric cap covering the trailing end of the second needle has been punctured. The logic consequences are that all vacuum tube holders, used more than once for blood collection, are likely to have their bores and second needle attachments contaminated with blood leakage from patients sampled sequentially. Simple peroxide, hypochlorite, steam, alcohol, autoclave, gamma-radiation or fluorine sterilizatuon of the vacuum tube holder after each use being impractical, it would seem simpler not to reuse such vacuum tube holders more than once or, at least provide protocols whereby reusable vacuum tube holders can be sustained reasonably clean. Because unit cost and disposable bulk factors are cogent, a further object of this invention is to disclose efficient, cost-effective use of reusable, as well as single use vacuum tube holders.

BRIEF DESCRIPTION OF THE DRAWINGS

FIG. 1 is a schematic side axial view of the integrated blood collection assembly before use. Scale here and in subsequent Figures is approximately 1:1.

FIG. 2 is a similar view, after a disposable leading needle scabbard has been removed and a vacuum tube has been inserted into the trailing end of the assembly.

FIG. 3 is a similar view, showing an inserted vacuum tube filled and the leading needle fully retracted into the leading part of the assembly by means of an extended slip connecter permanently embodied in the leading end of a vacuum tube holder.

FIG. 4 is a similar view, showing the assembly separated into two safely disposable parts by breaking a slip connection between the leading needle hub and the extended slip connector embodied in the leading end of the vacuum tube holder.

FIGS. 5a,b is a similar view, wherein a reusable vacuum tube holder is attached.

FIG. 6 is a similar view, showing the reusable vacuum tube holder attached and ready for use with the first inserted vacuum tube.

FIG. 7 is a similar view, showing the last inserted vacuum tube almost filled and the leading needle fully retracted into the leading part of the assembly by means of an extended slip connector temporarily attached to the leading end of the reusable vacutainer holder.

FIG. 8 is a similar view, showing the assembly separated into two parts by breaking a slip connection between the leading needle hub and the extended slip connector attached to the leading end of the reusable vacuum tube holder.

FIGS. 9a,b,c is a similar view, showing the assembly dissembled into two safely disposable parts, the reusable vacuum tube holder, and a blood-filled vacuum tube.

FIG. 10 is a similar view, showing needle scabbards for dispensing the assembly.

FIG. 11 is a plain axial view, showing lateral projections for first needle stabilization.

FIGS. 11–12 are views, showing additonal means for stabilizing assembly parts.

FIG. 13 is a lateral view, showing first stages of dissembly.

FIG. 14 is a plane view, showing fail-safe mechanisms via scabbard reuse.

DESCRIPTION OF THE PREFERRED EMBODIMENTS

FIG. 1 shows the integrated assembly for safe blood collection after unpacking for sterile use. The assembly essentially comprises a tubular needle holder 11 for a first needle 12 linked to a vacuum tube holder 13 permanently embodying a second needle 14, and an extended rigid transparent tube 15, whose conical beveled leading open end 16 is reversibly linked by means of a slip-connection into a mating bore 17 in the trailing end of the hub of the first needle 12, such that the extended rigid transparent tube 15 first serves sequentially as an axially centered needle guide directing the thrust of the first needle 12, a means for sensitively gauging accurate first needle intravenous insertion by blood flash back before a vacuum tube is inserted over the second needle 14 in the holder, as a means for retracting the entire first needle 12 into the bore of the tubular needle holder 11 and, in a second preferred embodiment disclosed later, as a means for safe disposal of the second needle 14.

The first needle holder 11 further comprises in trailing sequence:

(a) a small elongated conical nozzle 19, like that on a standard Luer-slip syringe, with an added head projection 20 for finger placement on the dorsal side of the nozzle facing the straight bevel 21 on the leading end of the first needle 12.

(b) a cylindrical leading end 22 whose bore is stopped by a tight elastomeric plug 23, shaped like a syringe piston without an inserted plunger, for further stabilizing the thrust of the first needle 12, putting a drag on that portion of the needle which passes therethrough, and preventing blood leakage of from the bore of the first needle holder 11 after the withdrawal of the first needle 12 therethrough.

(c) a conical trailing end 24 whose bore gradually decreases in internal diameter at a point distant from the trailing end of the tight elastomeric plug 23 substantially greater than the entire length of the first needle 12 and having an internal diameter less than the external diameter of a circular flange 25 on the hub of the first needle 12; and whose bore at the trailing end is just slightly greater in diameter than the external diameter of the extended rigid transparent tube 15.

The vacuum tube holder 13 embodying the extended rigid plastic tube 15 and forming the hub 26 of the second needle 14, in addition forms the base for an affixed tubular elastomeric cap 27 with a closed trailing end, a mid-portion which encloses the bevel and shank of the second needle and a leading open end which affixes by elastic recoil over the hub 26 of the second needle 14. As currently constructed, this needle penetrable tubular elastomeric cap offering little, if any protection from accidental needlesticks, primarily comprises an initially air-tight seal which prevents venous blood under 5–20 cm. of hydrostatic pressure from leaking into the bore of the vacuum tube holder 13 before a first vacuum tube is inserted and minimizes blood leakage into the bore after each use and final use of one or more vacuum tubes to withdraw blood for testing.

Finally, a needle scabbard 28 is reversibly attached over the leading conical nozzle 19 of the needle holder 11 for protecting the leading end of the assembly before venous insertion of the first needle 12.

FIG. 2 shows the assembly after the needle scabbard 28 has been removed, the first needle 12 has been accurately inserted through the skin into the selected vein of a patient (not shown), and the flash-back of venous blood 29 is observed in the bore of the rigid transparent tube 15. Then, a vacuum tube 30 with a penetrable cap 31 is inserted into the bore of the vacuum tube holder 13, such that second needle 14 penetrates through the cap 31 to establish fluid continuity between the first needle 12 and the second needle 14; and the tubular elastomeric cap 27 covering the second needle 14 is also penetrated and collapsed between the penetrable cap 31 and the hub 26 of the second needle 14. Not shown, but after filling of the first vacuum tube 20 inserted, and each successively inserted the tubular elastomeric cap will recoil back into the configuration shown in FIG. 1 to minimize the leakage of venous blood into the bore of the vacuum tube holder, even though the tubular elastomeric cap 27 may not remain air- or fluid-tight after needle puncture.

FIG. 3 shows the assembly during the process of shielding the first needle 12 when the last vacuum tube 30 inserted into the vacuum tube holder 13 is almost filled. In trailing sequence:

(1) Downward finger pressure in the direction of the arrows 31 over a sterile pledget 32 used to cover the venipuncture site and exert occlusive pressure on the underlying vein for assuring optimal hemostasis will simultaneously anchor the small elongated conical nozzle 19 on the leading end of the needle holder 11 against the skin overlying the venipuncture site, when backward movement of the elongated conical nozzle 19 is impeded by stop pressure translated to the trailing end of the dorsal head projection 20 on the elongated conical nozzle 19.

(2) With the leading end of the first needle holder 11 thus anchored, backward retraction of the vacuum tube holder 13 in the direction of the arrow 33, axially translated by means of the extended rigid transparent tube 15, will retract the entire first needle 12 into the bore of its holder 11 to a predetermined point of wedge impaction IP dictated by the external diameter of the circular flange 25 on the hub of the first needle 12 in relation to the decreasing internal diameter of the conical trailing portion 24 of the first needle holder 12.

As desired results of (1) and (2), the sharp bevel 21 and shank of the first needle 12 will become extracted from the selected vein at an optimized angle of withdrawal and safely confined by wedge impaction of its hub 17 in the bore of the first needle holder 11, without exposure of the bevel or shank during or after venous withdrawal. It should be noted, further, that the process of first needle withdrawal from the selected vein is precisely like a user would withdraw a 3.0 mL. syringe-attached needle from a vein by holding pressure over the venipuncture site with a finger of the non-dominant hand holding a pledget holding pressure down over a pledget to optimize hemostasis and pulling back on the syringe barrel simultaneously with the other hand. However, in order to withdraw the needle without exposure into the first needle holder, a user will pull the vacutainer holder back with the dominant hand, preferably before the vacuum in the vacuum tube is exhausted and the last vacuum tube is removed from the holder, such that most of the blood in the first needle 12 and the extended rigid transparent tube 15 will be cleared from the blood conveying bore of the system and not prone to drip.

FIG. 4 shows the assembly after the circular flange 25 on the first needle hub 17 has been wedge impacted IP into the bore of the trailing conical portion 24 of the first needle holder 11 and, then, further retraction with rotation in the direction of arrow 41 of the extended rigid transparent tube 15 embodied into the vacuum tube holder breaks the slip-fit connection between the trailing portion of the first needle hub 17 and the mating male counterpart 16 on the leading end of the extended rigid transparent tube 15. This manual maneuver performed with the dominant hand, while the non-dominant hand continues to hold pressure over the venipuncture site and the dorsal head projection 20 on the elongated conical nozzle 19, separates the assembly into two parts, each containing a shielded safely disposable needle, after the last vacuum tube is removed from the vacutainer holder.

Because it is questionable whether blood contamination of the bore of the vacuum tube holder after one or more insertions of vacuum tubes for collecting blood, and single use of a vacuum tube holder might seen costly, a second preferred embodiment of the assembly is described in FIGS. 5a–b to 9a–c, along with alternative means in the leading end of the first needle holder for consummating stable exposure of the bevel and shank of the first needle during venous insertion and stabilizing the leading end while holding downward finger pressure over a selected vein to optimize hemostasis and minimize vein injury during first needle withdrawal.

FIG. 5a shows an alternative assembly designed for use with a separate vacutainer holder 51 shown in FIG. 5b into which one more vacuum tubes 30 may be sequentially inserted by means of the assembly shown in FIG. 5a for collecting venous blood. This assembly, then, comprises the needle holder 11 for a first needle 12 and a rigid transparent tube 15 whose conical beveled leading open end 16 is reversibly linked by a slip-connection into a mating bore 17 in the trailing end of the hub of the first needle 12. The trailing end of rigid transparent tube 15 which extends through the open end of a conical trailing portion 24 of the first needle holder 11 further comprises an externally threaded part 52 matching internal threads 53 in the leading open end of the vacuum tube holder 51 and holds a terminally trailing second needle 14 covered by an elastomeric cap 55 anchored on the terminal end of the rigid transparent tube 15.

The first needle holder 11 further comprises a leading elongated conical hollow nozzle 19 with a dorsal head projection 20 for finger placement, as structurally and functionally described under FIG. 1. However, this second preferred embodiment differs in that the bore of the hollow nozzle 19 is plugged by a leading conical portion 54 on the hub 17 of the first needle 12, such that a reversible slip-fitting connection is established, wherein rotation of the needle hub is precluded by matching ridges on the apposing conical surfaces (not shown).

Aside from a trailing disposable scabbard 55 for protecting the bevel and shank of the second needle, all remaining labeled parts of the assembly are structurally and functionally similar to those designated under descriptions of FIGS. 1–3, even though the first needle holder shapes may appear more streamlined in FIGS. 5–8 and appear to engender a more optimal angle of first needle insertion and withdrawal. It should be noted that a - - - a' in FIG. 5a marks a possible site where the leading 11 and trailing 24 portions of the first needle holder might be permanently joined and bonded during fabrication of the assembly.

In Brief Temporal Recapitulation

FIG. 6 shows the assembly poised for drawing venous blood into the first inserted vacuum tube 30, after (a) removal of the protective scabbard 28 for the first needle 12; (b) insertion of the bevel and shank of the first needle 12 into a selected vein, using the dominant hand to grasp and manipulate the leading end of the first needle holder 11 like a standard 3.0 mL. syringe; (c) removing the protective scabbard 55 for the second needle 14, after flash-back 29 of venous blood is visible in the rigid transparent tube 15; (d) screw-on attachment 52–53 of the trailing end of the rigid transparent tube 15 to the leading end of the vacuum tube holder 51; and (e) insertion of the vacuum tube 30 into the temporarily attached vacuum holder 51, such that the leading penetrable cap 31 of the vacuum tube 30 is penetrated by the bevel and part of the shank of the second needle 14. Not shown in this Figure or in FIG. 2 is that during insertion and withdrawal of each vacuum tube subsequently inserted, the user must firmly hold the vacuum tube holder 51 or 13 with one hand while manipulating vacuum tubes with the other, such that the attached rigid transparent tube 15 connecting the hubs of the first needle 12 and second needle 14 are not significantly displaced backward or rotated during the process.

FIG. 7 shows the assembly during the safe shielding of the first needle 12 in the bore of the first needle holder 11, before the last vacuum 30 tube is withdrawn from the vacuum tube holder 51, as described in more mechanical detail under FIG. 3. In sequence, the user holds finger pressure 31 over pledget 32 covering the dorsal head projection 20 on the leading nozzle 19 of the first needle holder 11 with a finger of the non-dominant hand, while retracting the vacuum tube holder 51 in the direction of the arrow 33 with the dominant hand to pull the circular flange 25 on the first needle hub 17 into a point of wedge impaction IP. Next, after the remaining vacuum in the last inserted vacuum tube has cleared most of the blood from the bore of the leading needle 12, the rigid transparent tube 15 and the trailing needle 14, the filled vacuum tube 30 is removed with the dominant hand or left in place, while the non-dominant hand continues to hold pressure over the dorsal head projection 20 to assure optimal hemostasis and anchor the leading end of the first needle holder 11. Next, as shown in FIG. 8, still holding finger pressure over the dorsal head projection 30 and underlying pledget 32, the first needle holder 11 with the entire needle 12 in its bore is disengaged from the vacuum tube holder 51 by further retraction 41 and clockwise rotation 81 of the temporarily attached rigid transparent tube whose beveled leading end 16 slip-connects with its mating part in the trailing end in of the first needle hub 17.

It should be interjected here that, contrasted with the first preferred embodiment of this blood collection assembly wherein the rigid transparent tube 15 and vacuum tube holder 13 are embodied in one piece, in the second preferred embodiment wherein the trailing end of rigid transparent 15 tube screws temporarily into the leading end of the vacuum tube holder 51 via conventional right-hand threads, clockwise rotation 81 of the assembled parts is essential to preventing premature separation. Counter-clockwise rotation is essential to their separation.

FIGS. 9a,b,c show the final configuration of the remaining parts of the assembly, after the first needle 12 entirely confined in the first needle holder 11 becomes compactly and safely disposable into a sharps container sooner or later. a. shows the rigid transparent tube 15 holding the second needle 14, exposed only after counter-clockwise unscrewing of trailing external threads 52 from mating internal threads 53 on the leading end of a simple reusable vacuum tube holder 51 shown in b. Safe disposal of the second sharp needle 14, then, becomes a matter of convenience implemented by counter-clockwise unscrewing of the trailing end of the rigid transparent tube 15 from the leading end of the reusable vacuum tube holder 51, when it is convenient to do so. c. shows the ultimate product - - - one or more vacuum tubes 30 safely and conveniently filled with venous blood.

FIGS. 10–15 show modifications of the second preferred embodiment wherein the vacuum tube holder can be reused, the leading end of the rigid tube 15 is permanently bonded into, instead of slip connected into the trailing end of the first needle hub 17, and other modifications for convenient and safer use are shown. FIG. 10 shows modification of the first needle scabbard 101, the second needle scabbard 102 and hub 103 of the second needle 14 to provide a convenient sterile package for the blood collection assembly. Essentially, the open ends of each scabbard abut over the second needle hub 103 to seal the assembly and provide a convenient place for adding a wrap-around label (not shown), as was standard in prior art for packaging unprotected first and second needles attached to a single hub. A needle bevel shield 104, as disclosed in U.S. Pat. No. 5,549,568, is added for preventing tangential needle stick injuries to patients and users when the second needle 14 with its elastomeric tubular cover 27 is exposed after withdrawal from a vacuum tube holder. Finally, it will be noted that the trailing end of the rigid tube 15 is expanded to form a cone 105 which slip connects over the trailing open end of the first needle holder 11, such that forward displacement of the latter 11 over the rigid tube 15 is appropriately controlled during venous insertion of the first needle 12.

FIG. 11 is plane axial view of the assembly showing the addition of paired lateral projections 111 for finger placement on the first needle holder 11, such that the user can stable hold and accurately guide the first needle bevel up into the vein of a patient. In addition, this figure shows attachment of a pediatric vacutainer holder 116 of relatively small external diameter to the hub of the second needle holder 103. Also, it will be noted in this plane view, that a ridge 112 is added to the hub of the second needle holder 103 to fit a corresponding notch 121 in the trailing end of the first needle holder 11 which is shown in side view in FIG. 12. The purpose of ridge to notch mating is, first, to sustain proper alignment of the head projection 20 toward the first needle bevel during and after venous insertion of the first needle, as shown in FIGS. 2–3 and 7–8; and, second, to additionally hamper forward displacement of the first needle holder 11 over the rigid tube 15 during venous insertion of the first needle 12.

FIG. 13 is a side view of the assembly showing the hub 17 of the first needle 12 needle wedge impacted IP in the bore of the first needle holder 11 by means of traction in the direction of the arrow 131, and the second needle 14 is partially protected by the bevel shield 104 in the trailing end of its tubular elastomeric cover 27.

FIG. 14 is a plane view showing additional options for user and patient safety when a sharps container is not immediately convenient after the assembly has been used for blood collection. Normally, the user would leave the vacuum tube holder 116 connected to the second needle hub 103 to protect the second needle 14 and, then, employing one hand to hold the exposed portion of the rigid tube 15 and the other to unscrew the vacuum holder 116, the user would retain the vacuum tube holder and drop the used assembly directly into a sharps container. However, when an appropriate sharps container is inconvenient, the first fail-safe move should be replace the first needle scabbard 101 over the shielded needle such that the open end of the first scabbard 101 engages the second needle hub 103 and leave the used vacuum tube holder 116 attached, such that the second needle 14 remains protected until detachment becomes convenient. If the vacuum tube holder 116 inadvertently falls off, the sharp bevel of the second needle 14 will remain partly protected from causing injuries from any side except straight on. Therefore, a one-handed recapping by means of the second needle scabbard 102 might seem appropriate, as shown here.

The dashed line b - - - b' in FIG. 14 indicates a possibly convenient site for bonding the conical leading end 19 with the head projection (not shown the is view) to the body of the first needle holder 11 during manufacture. It will be noted that the aperture in the leading end of the conical nozzle 19 appears substantially larger than the external diameter of the bevel and shank of the first needle 12. in FIGS. 10–14. These Figures were drawn so, partly to indicate that hollow bore steel needles commonly used for blood collecttion usually vary from 23 G to 19 G. Therefore, it might seem advantageous for manufactureres to apply leading nozzles of differing bores at b - - - b' during the closure of the leading end of the first needle holder 11 with a dorsal head projection 20 and paired lateral additions for finger placement 111.

Another feature in the assembly, not obvious in the drawings, is that owing to the acute angle of venous access and egress, the exposed part of the first needle 12 need not be of a standard 1.0" in length. A shorter exposed bevel and shank of the needle 12 which allows the dorsal head projection 20 on the leading nozzle 19 of the first needle holder 11 to approach as close as possible to the actual venipuncture site will prove most efficient for blood collection with the least likelihood of producing venous injury. Secondarily, if a shorter first needle is embodied, the first needle holder 12 will be correspondingly shorter and require appropriate packaging.

With respect to packaging, the form shown in FIG. 1 having a leading disposable scabbard 27 for sterile protection of exposed parts of the first needle 12 inserted into the packaging system for the entire assembly shown in FIG. 10 would seem optimal for convenience, as well as patient and user safety. In summation, then, the final goal of minimizing exposure to exposed parts of the first and second needles, except when needed for actual intended use will be approached.

Finally, the first, second and third embodiments, as specified, are only exemplary and not intended to be limiting. It will be appreciated by those skilled in the art that wide variations in details can be made without departure from the spirit of the invention.

Therefore, I claim:

1. A needle assembly operable for the transfer of blood from a blood vessel to a vacuum tube contained within a vacuum tube holder comprising:

(a) a first needle holder having a leading end and a trailing end and a hollow conical body portion therebetween, said hollow conical body portion having a conical cavity therewithin;

(b) a first hollow bore needle having a sharp beveled tip at a leading end thereof, a hub at a trailing end thereof, and a shank therebetween, said hub being disposed within said conical cavity and releasably attached to said leading end of said first needle holder;

(c) a rigid tube having a leading end affixed to said hub of said first needle, a trailing end and a length therebetween, said rigid tube having an axial bore coextensive with said length;

(d) a second hollow bore needle having a leading end disposed within said axial bore of said rigid tube and affixed to said trailing end of said rigid tube, said second needle having a trailing portion comprising a sharp trailing end projecting from said trailing end of said rigid tube, said trailing portion further comprising attachment means operable for releasably attaching said second needle to the vacuum tube holder.

2. The needle assembly of claim 1 wherein said first needle holder further comprises stabilization means on the leading end thereof, said stabilization means on the leading end thereof being operable for receiving a finger placed thereon, thereafter holding said first needle holder in slip resistant contact with a patient's skin when traction is applied to said trailing end of said rigid tube.

3. The needle assembly of claim 1 further comprising a first needle cap releasably connected to said trailing end of said rigid tube and disposed to enclose said sharp beveled tip and shank of said first hollow bore needle.

4. The needle assembly of claim 1 further comprising a second needle cap releasably connected to said trailing end of said rigid tube and disposed to enclose said sharp trailing end of said second hollow bore needle projecting from said trailing end of said rigid tube.

5. The needle assembly of claim 1 wherein said trailing portion of said rigid tube is nonreleasably affixed to said vacuum tube holder.

* * * * *